United States Patent [19]

Ott

[11] 4,107,775

[45] Aug. 15, 1978

[54] HUMAN BODY COMPARISON USING DRIVING POINT PARAMETERS

[75] Inventor: James H. Ott, Akron, Ohio

[73] Assignee: Novar Electronics Corporation, Barberton, Ohio

[21] Appl. No.: 667,287

[22] Filed: Mar. 16, 1976

[51] Int. Cl.² ............................................. G06F 1/00
[52] U.S. Cl. ................................. 364/413; 73/579;
128/2 R; 181/126; 340/149 R; 364/576;
364/900
[58] Field of Search ...................... 235/151.3, 61.7 R;
340/172.5, 149 R, 146.2; 445/1; 128/2 V, 2 R,
2.1 Z, 24 A; 73/67.2; 181/126, .5; 324/57 R;
364/200, 900 MS File, 413, 400, 576

[56] References Cited

U.S. PATENT DOCUMENTS

| Re. 29,008 | 10/1976 | Ott | 340/172.5 |
|---|---|---|---|
| 3,477,422 | 11/1969 | Jurist, Jr. et al. | 73/67.2 |
| 3,639,905 | 2/1972 | Yaida et al. | 235/61.7 R |
| 3,872,443 | 3/1975 | Ott | 340/172.5 |
| 3,958,559 | 5/1976 | Glenn et al. | 128/24 A |
| 3,990,436 | 11/1976 | Ott | 73/67.2 |

*Primary Examiner*—Malcolm A. Morrison
*Assistant Examiner*—Errol A. Krass
*Attorney, Agent, or Firm*—Frank H. Foster

[57] ABSTRACT

An apparatus and method suitable for automatic machine interrogation of individuals for identifying or analyzing persons such as those seeking admittance to secure areas or seeking an extension of credit. Physical vibration wave energy is applied by a signal generator and transducer to the person's body at a selected point such as the finger tips. The frequency and/or the time function of force and/or motion parameters at the driving point of the body are then detected and stored. Comparison of a previously known function with a subsequently measured function to determine whether they are within preselected tolerances permits a machine decision whether the functions represent the same person.

25 Claims, 1 Drawing Figure

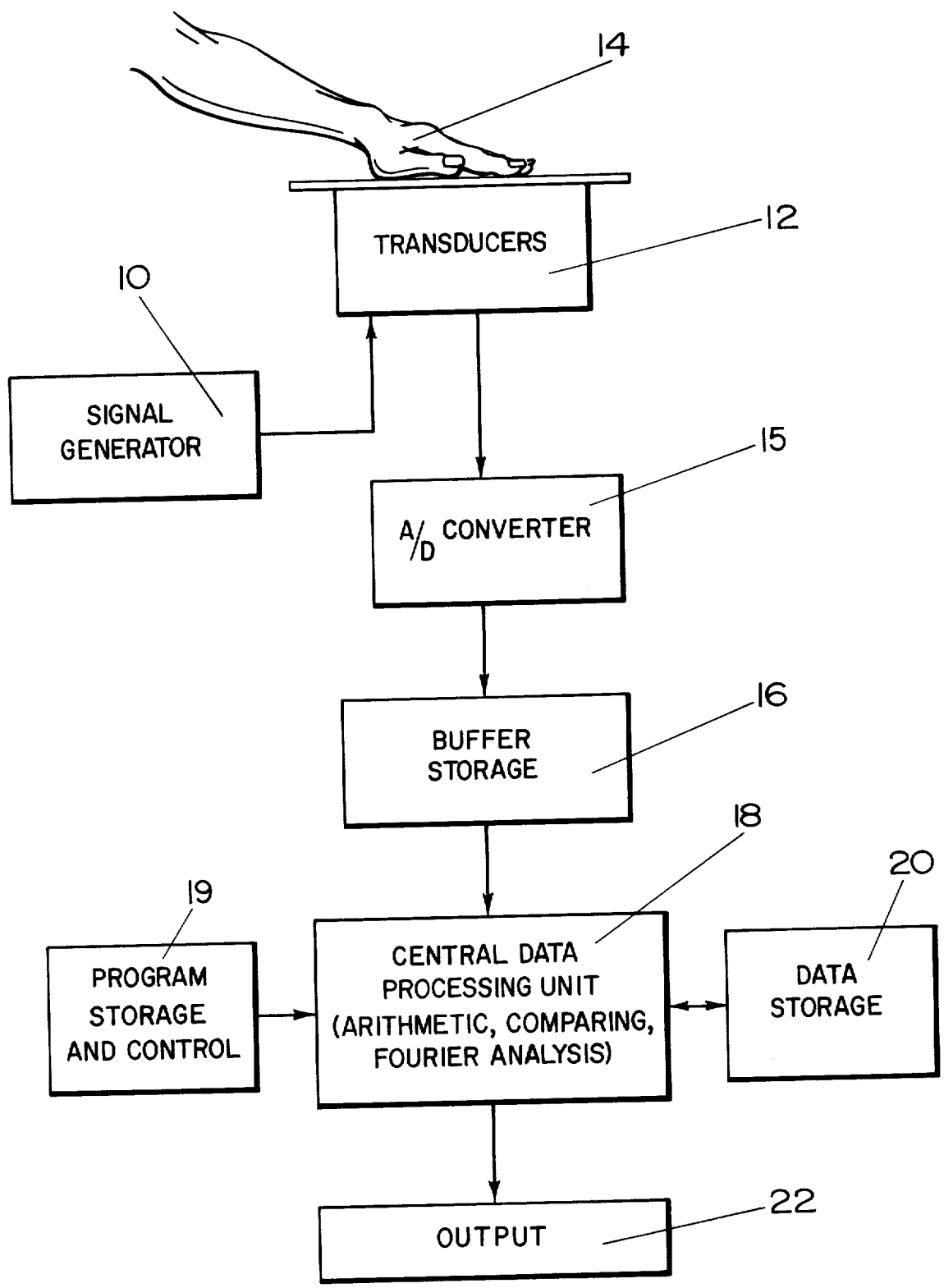

HUMAN BODY COMPARISON USING DRIVING POINT PARAMETERS

BACKGROUND OF THE INVENTION

This invention relates to machine identification or analysis of persons and more particularly relates to a method and apparatus for computer measurement and analysis of the frequency domain and/or time domain characteristics of a person's body at a selected point for automatically identifying or comparing that person to a previously machine interrogated person.

The computer industry is presently engaged in developing systems for rapid, accurate and automatic computer identification and analysis of persons.

A typical use for such a system would be to automatically identify persons seeking admittance to a secure area in a plant or to sensitive data stored in a computer memory. For example, a person seeking sensitive data or admittance to a secure area would be interrogated by a computer to determine if he is a person authorized to have access to such area or data. An apparatus embodying the invention can form a computer controlled lock.

Similarly, machine identification would be used in credit transactions, such as is currently being planned for future use. In such a transaction, a person would not only present his credit card to a clerk, but in addition, would be subjected to machine identification for a determination that he is the person who owns the card being presented. Such a system can reduce the damages from credit card losses and theft.

I have discovered a method and apparatus for individual identification involving the application of physical vibration wave energy to a person's body and the subsequent detection of the frequency and/or time function of the motion and force variations created at the point of applying the wave energy and the comparing of data representing these variations which were detected at different times.

Others have applied physical vibration wave energy to a person's body. For example, sonic energy is applied to provide a "picture" of the internal condition of the body for medical purposes. Such systems apply sonic energy in a radar type system or in a holographic system. Although these systems apply sonic energy to the human body, this is their only similarity to the present invention. The prior art methods and apparatus for obtaining and for processing the received energy differ greatly from that used in the present invention. In the system of the present invention, a comparison is made of the mechanical force and/or motion characteristics. In these prior art systems, radar or sonar principles are used to obtain "pictures".

Still others have applied an impulse, such as a step function or single pulse, to a human tooth to look at its undriven, resonant characteristics. However, I neither apply an impulse nor do I detect undriven resonant vibrations. With my invention a computer will be able to identify the person operating it so that data will be accessible to this person. Compact locking devices may be programmed to admit only certain individuals. A computer can interrogate and identify a person over the telephone. For example, the identity of a salesman wanting computer data from a distant city in a motel through an acoustical coupler can be quickly and accurately verified. Credit cards and checks may contain a coding which would permit a quick identity verification at point of purchase with a simple machine. Automobiles can be programmed to operate for only specific individuals. Homes, apartments, or any secured property can be made accessible only to owners. Legal signatures can be obtained by telephone by permitting the identification to function as a legal signature.

Analysis according to the present invention may also be adopted for use in the medical field. For example, a new means may be at hand which will provide a quick and simple check for bone or soft tissue condition. It may even be possible to determine the emotional state or tension of the person whose identity has been established. This can be important where a person who is authorized to remove information from the computer might be nervous because he is intending to do this for illegitimate reasons or is under duress.

SUMMARY OF THE INVENTION

The invention is an apparatus and a method for analyzing and/or identifying individual persons. The system applies non-impulsive, physical vibration wave energy to a selected driving point on a human body at a plurality of frequencies and detects and stores data representing force and/or motion variations as a function of time and/or frequency at said point while said wave energy is being applied. At a subsequent time the system does the same thing to a subsequent person and then compares the two sets of data to determine whether they are within selected tolerances.

Accordingly, it is an object of the invention to provide an identification and analysis method and apparatus suitable for automatic machine use.

Further objects and features of the invention will be apparent from the following specification and claims when considered in connection with the accompanying drawings illustrating several embodiments of the invention.

DESCRIPTION OF THE DRAWINGS

The FIGURE is a diagram illustrating an embodiment of the invention.

In describing the invention as illustrated in the drawings, specific terminology will be resorted to for the sake of clarity. However, it is not intended to be limited to the specific terms so selected and it is to be understood that each specific term includes all technical equivalents which operate in a similar manner to accomplish a similar purpose. For example, use of the word "connection" includes not only direct connection, but also connection through an intermediate circuit where such a connection is equivalent as known by those skilled in the art.

DETAILED DESCRIPTION

Referring to the FIGURE, a signal generator 10 is used to generate the signal to be applied to the body of a person. Although various portions of the frequency spectrum may be useful, I believe that the sonic and near ultrasonic portion of the spectrum is most useful in the preferred embodiment of the invention.

The signal generator 10 generates a non-impulsive wave of electrical energy at a plurality of frequencies. By non-impulsive I mean that it does not generate a step function or a single pulse. It may, however, for example, generate a white noise signal, a signal consisting of a plurality of selected sinusoids, a frequency sweep either continuous or time-spaced, sequentially-applied, discrete frequencies, periodic bursts of wave energy such as the above, or a train of impulses which preferably are periodic.

These electrical signals from the signal generator 10 are applied to a transducer 12 to convert the signals to physical vibration wave energy which are then applied by the transducer 12 to a selected driving point on the human body, such as a human hand 14 illustrated in the FIGURE.

Because the human body is a mechanical body the applied wave energy will generate force and motion variations at the driving point in a manner similar to the generation of stress and strain in a rigid elastic body.

The force and motion as a function of time and/or frequency is determined in part by the drive signal and in part by the characteristics of the human body part. It is the purpose of the present invention to detect and compare data which represent the body part characteristics at the driving point of an initially interrogated body part with the driving point characteristic of a subsequently interrogated body part. Of course the comparing step may include the performance of a variety of mathematical operations on the data such as, for example, averaging or integrating.

The most commonly examined motion parameters are displacement, velocity, and acceleration. As is very well known, each of these is obtainable by one or two appropriate integrations or differentiations of any other one.

The prior art is filled with force, displacement, velocity and acceleration transducers for measuring force and motion of the types described. They may, for example, be found in the ISA compendium and in many other places in the prior art.

Consequently the transducer 12 may comprise not only a transducer for applying the signal from the signal generator 10 to the body 14, but may additionally comprise one or more of the known prior art transducers for detecting force and/or motion variations.

Alternatively, variation data of force and motion may be obtained from the voltage and current applied to a single drive transducer. For example, if the signal generator 10 generates a known voltage signal, then current flow through the transducer and the apparent electrical impedance of the transducer will have a known correspondence with the force and motion variations at the driving point. Such correspondence is described in the prior art particularly in the field of sonic devices.

It should be noted that certain ratios of force and motion measurements have been defined in the prior art. For example, the ratio of force to velocity is defined as the mechanical impedance and its reciprocal is known as the mobility of the mechanical body at the driving point. Similarly, the ratio of force to acceleration is defined as the apparent mass and its reciprocal is known as the inertance. In a similar manner the prior art defines the ratio of force to displacement as the apparent stiffness and its reciprocal as the compliance of the mechanical body. Alternatively, instead of utilizing such ratios a product of force and one of the motion parameters may be determined in units of power.

For purposes, however, of the present invention it is necessary to generate force and motion variations at the driving point and to detect at least one and preferably the force and one of the motion variations as a function of time or frequency. The force and motion variations may be detected by means of known transducers or alternatively derived from the input conditions of the driving transducer. I prefer to detect a ratio of force to a motion parameter and particularly to detect the impedance as a function of time and/or frequency.

The transducer 12 which applies the signal to the body part 14 may, for example, consist of a piezoelectric transducer or a vibrator which consists of a coil mechanically linked to a diaphragm and suspended in a magnetic field so that it will move upon excitation of the coil by the signal generator 10. With the latter device, the applied force is proportional to the current through the vibrator.

The usual transducer encountered in the prior art would apply or generate waves which propogate along an axis perpendicular to the body part/transducer interface. These would generate compression waves in the human body at the driving point. However, it should be understood that vibrations contemplated by the present invention may also be generated in other directions. They may, for example, be generated parallel to the transducer/body part interface or at some oblique angle to it.

In referring to time and/or frequency dependent functions I am referring to the well known Fourier transformations which permit a signal to be considered and examined in either the time domain or frequency domain as is well known in the art. Whether a signal is considered with respect to time or to frequency, it is still the same signal. The detected variation signals can be arithmetically or otherwise operated upon by known electronic computing elements to multiply or divide any one by another in analog or digital form and are also capable of undergoing a machine Fourier transform. Hewlett-Packard and others sell Fourier analyzers.

I prefer however to detect the signals from the transducer or transducers indicated as 12 and convert them to digital form by means of a conventional analog to digital converter 14. The transducer signals which are applied to the analog to digital converter are detected while the wave energy is being applied to the body part. Therefore, the output of the transducers 12 provides a first set of data representing at least one of the above mentioned variations as a function of time or frequency. When converted to digital form these may be stored in a buffer storage 16.

Data from the initial or first interrogation of the body part at a driving point may be processed by a simple data processing unit 18 and stored in a data storage 20 for subsequent reference.

These data might for example consist of a plurality of signal samples taken during a selected time interval while the body part is being driven by the applied physical vibration wave energy. These samples might be time spaced samples of signal amplitude or alternatively, for example, they might be amplitude samples for a plurality of different frequencies in the spectrum of the applied physical vibration wave energy.

The central data processing unit can also perform the desired operations to obtain the ratio or product which is described above if a ratio or product is desired and is not directly obtainable from the particular transducer chosen.

At a subsequent time a similar physical vibration wave energy signal is applied to a subsequent person at a corresponding driving point such as the hand and a second set similar data is derived in the same manner.

This data may, for example, be stored in the buffer storage and it is then compared with the initially detected data in data storage 20 to determine if the two sets of data are within selected tolerances of each other.

For example, and only by way of example, amplitude samples described above or samples representing the ratio of variations defined as the impedance sampled at a selected plurality of frequencies such as at every 100 Hz, may be obtained and appropriately stored. The comparator unit of the central data processing unit may then compare corresponding samples at identical frequencies (or times) one by one in sequence to determine whether they are for example within 10% of being equal. The processing unit can count the number of samples which are within 10% of each other and the number which are not within 10% and then determine whether, by way of example, at least 90% of the samples are within 10% of each other. It they are then the two stored sets of data may be considered as being identical and the unit may then signal such by its output 22.

Of course several different transducers for detecting several force and motion variations at the driving point can be collected, converted to digital form and stored in different records. These would permit a greater variety of more complex comparison operations.

The details of the computer processing and storing apparatus and the programming for accomplishing this are not disclosed since they would be routine to a person skilled in data processing arts upon reading the above description.

It is to be understood that while the detailed drawings and specific examples given describe preferred embodiments of the invention, they are for the purposes of illustration only, that the apparatus of the invention is not limited to the precise details and conditions disclosed and that various changes may be made therein without departing from the spirit of the invention which is defined by the following claims.

I claim:

1. A method for comparing a subsequently interrogated person with a previously interrogated person, the method comprising:
   (a) applying non-impulsive, physical vibration wave energy to a selected driving point on a human body at a plurality of frequencies to generate force and motion variations at said driving point;
   (b) detecting a first set of data, while said wave energy is being applied, which data represents at least one of said variations as a function of time at said driving point;
   (c) storing said first set of data;
   (d) subsequently applying non-impulsive, physical vibration wave energy to a subsequent, corresponding driving point on a human body at a plurality of frequencies to generate subsequent force and motion variations at said subsequent driving point;
   (e) detecting a second set of data, while said wave energy is being applied, said second set of data representing at least one of said subsequent variations as a function of time at said subsequent driving point; and
   (f) comparing said first set of data with said second set of data to determine whether they are within selected tolerances of each other.

2. A method according to claim 1 wherein said sets of data represent a product of motion and force variations as a function of time.

3. A method according to claim 1 wherein said sets of data represent a ratio of force and motion variations as a function of time.

4. A method according to claim 3 wherein said ratio is the driving point impedance.

5. A method according to claim 1 wherein said generated variations comprise essentially compressional waves.

6. A method according to claim 1 wherein said data is detected by sampling the analog form of said variations at said driving point and converting them to a plurality of digital samples at selected time intervals.

7. A method according to claim 6 wherein each of the samples of said first set of data are compared to corresponding samples of each of the samples of said second set of data.

8. A method according to claim 6 wherein said samples are machine converted by a Fourier transform to a plurality of samples at selected frequencies.

9. A method according to claim 1 wherein said detected motion variation data is data representing displacement.

10. A method according to claim 1 wherein said detected motion variation data is data representing velocity.

11. A method according to claim 1 wherein said detected motion variation data is data representing acceleration.

12. A method for comparing a subsequently interrogated person with a previously interrogated person, the method comprising:
   (a) applying non-impulsive, physical vibration wave energy to a selected driving point on a human body at a plurality of frequencies to generate force and motion variations at said driving point;
   (b) detecting a first set of data, while said wave energy is being applied, which data represents at least one of said variations as a function of frequency at said driving point;
   (c) storing said first set of data;
   (d) subsequently applying non-impulsive, physical vibration wave energy to a subsequent corresponding driving point on a human body at a plurality of frequencies to generate subsequent force and motion variations at said subsequent driving point;
   (e) detecting a second set of data, while said wave energy is being applied, said second set of data representing at least one of said subsequent variations as a function of frequency at said subsequent driving point; and
   (f) comparing said first set of data with said second set of data to determine whether they are within selected tolerances of each other.

13. A method according to claim 12 wherein said sets of data represent a product of motion and force variations as a function of frequency.

14. A method according to claim 12 wherein said sets of data represent a ratio of force and displacement variations as a function of frequency.

15. A method according to claim 14 wherein said ratio is the driving point impedance.

16. A method according to claim 12 wherein said generated variations comprise essentially compressional waves.

17. A method according to claim 12 wherein said data is detected by sampling the analog form of said variations at said driving point and converting them to a plurality of digital samples at selected frequencies.

18. A method according to claim 17 wherein each of the samples of said first set of data are compared to corresponding samples of each of the samples of said second set of data.

19. A method according to claim 17 wherein said samples are machine converted by a Fourier transform to a plurality of samples at selected time intervals.

20. A method according to claim 12 wherein said detected motion variation data is data representing displacement.

21. A method according to claim 12 wherein said detected motion variation data is data representing velocity.

22. A method according to claim 12 wherein said detected motion variation data is data representing acceleration.

23. An apparatus for comparing a subsequently interrogated person with a previously interrogated person, said apparatus comprising:

(a) means for applying non-impulsive, physical vibration wave energy to a selected driving point on a human body at a plurality of frequencies to generate force and motion variations at said driving point;
(b) means for detecting a set of data representing at least one of said variations as a function of time or frequency at said driving point;
(c) means for storing said data; and
(d) means for comparing data detected at a first time at said driving point to data detected at a subsequent time at a corresponding driving point to determine whether said sets of data are within selected tolerances of each other.

24. An apparatus according to claim 23 wherein said detecting means comprises a force transducer and a motion transducer.

25. An apparatus according to claim 24 wherein said motion transducer comprises a velocity transducer.

* * * * *